United States Patent [19]

Urquhart et al.

[11] 4,436,741

[45] * Mar. 13, 1984

[54] METHOD FOR ADMINISTERING SCOPOLAMINE TRANSDERMALLY

[75] Inventors: John Urquhart; Santosh K. Chandrasekaran, both of Palo Alto; Jane E. Shaw, Atherton, all of Calif.

[73] Assignee: ALZA Corporation, Palo Alto, Calif.

[*] Notice: The portion of the term of this patent subsequent to Apr. 14, 1998 has been disclaimed.

[21] Appl. No.: 474,754

[22] Filed: Mar. 14, 1983

Related U.S. Application Data

[60] Continuation of Ser. No. 253,961, Apr. 13, 1981, abandoned, which is a continuation of Ser. No. 777,130, Mar. 14, 1977, Pat. No. 4,262,003, which is a division of Ser. No. 721,602, Sep. 7, 1976, Pat. No. 4,031,894, which is a continuation-in-part of Ser. No. 638,947, Dec. 8, 1975, abandoned, which is a continuation-in-part of Ser. No. 547,504, Feb. 6, 1976, abandoned.

[51] Int. Cl.$^3$ ............................................ A61K 31/445
[52] U.S. Cl. ..................................................... 424/267
[58] Field of Search ......................................... 424/267

[56] References Cited

U.S. PATENT DOCUMENTS 3,797,494  3/1974  Zaffaroni ............................ 128/268
3,996,934  12/1976  Zaffaroni ............................ 128/268

Primary Examiner—Frederick E. Waddell
Attorney, Agent, or Firm—Steven F. Stone; Edward L. Mandell; Paul L. Sabatine

[57] ABSTRACT

Method and therapeutic system in the form of a bandage that administer scopolamine base transdermally in an initial pulse of 10 to 200 $\mu$g/cm$^2$ of skin that quickly brings the concentration of scopolamine in the plasma to a level at which emesis and nausea are inhibited without intolerable side effects, followed by a substantially constant dosage in the range of 0.3 to 15 $\mu$g/hr that holds said level. The bandage is a four-layer laminate of, from the top: a protective backing; a gelled, mineral oil-polyisobutene-scopolamine reservoir lamina that is the source of the constant dosage; a microporous membrane that controls the constant dosage rate; and a gelled, mineral oil-polyisobutene-scopolamine adhesive layer that is the source of the pulse dose and the means by which the bandage is attached to the skin.

11 Claims, 1 Drawing Figure

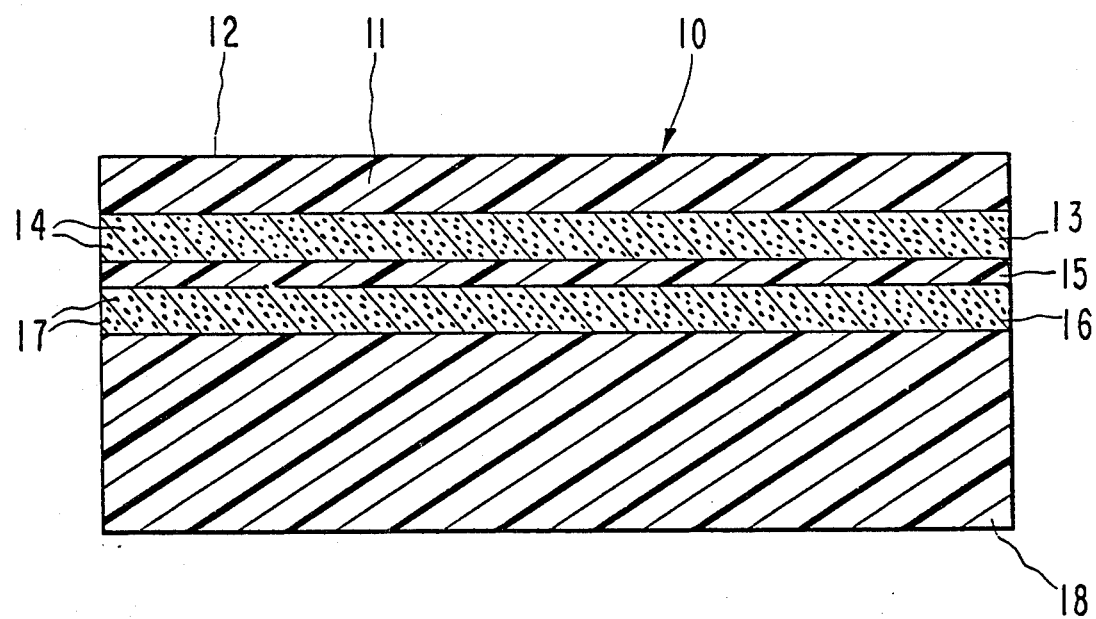

METHOD FOR ADMINISTERING SCOPOLAMINE TRANSDERMALLY

CROSS-REFERENCE TO RELATED APPLICATION

This application is a continuation of Ser. No. 253,961, filed Apr. 13, 1981, now abandoned, which in turn is a continuation of Ser. No. 777,130 filed Mar. 14, 1977, now U.S. Pat. No. 4,262,003, which is a divisional of Ser. No. 721,602 filed Sept. 7, 1976 now U.S. Pat. No. 4,031,894, which is a continuation-in-part of Ser. No. 638,947 filed Dec. 8, 1975, now abandoned, which is a continuation-in-part of Ser. No. 547,504 filed Feb. 6, 1976, now abandoned.

BACKGROUND OF THE INVENTION

1. Field of the Invention

The invention is a method for administering scopolamine transdermally to inhibit emesis and nausea and a therapeutic system in the form of a bandage structured specifically to carry out the method.

2. Description of the Prior Art

There are several patents that relate to bandages for administering systemic drugs transdermally. In this regard, U.S. Pat. No. 3,797,494 is believed to be the most relevant to the present invention. FIG. 2 of that patent shows a bandage that includes the basic elements of the invention bandage. Indeed, the invention bandage is considered to be a patentable embodiment of the bandage depicted in said FIG. 2. Both bandages are laminates that include a backing, a drug reservoir, a microporous membrane and a contact adhesive layer. However, scopolamine is present in the invention bandage in specific proportions in the contact adhesive layer as well as in the reservoir. Also, the matrix of the reservoir layer of the invention bandage is a gel.

The antiemetic and antinauseant properties of scopolamine and related compounds are known. These properties have been investigated by administering scopolamine and related compounds intramuscularly and orally.[1]

[1] C. D. Wood and A. Graybiel, "Theory of Antimotion Sickness Drug Mechanisms," Aerosp. Med. 43: 249–52, 1972; and C. D. Wood and A. Graybiel, "A Theory of Motion Sickness Based on Pharmacological Reactions," Clin. Pharm. 11: 621–9, 1970; J. J. Brand and P. Whittingham, "Intramuscular Hyoscine in Control of Motion Sickness," Lancet 2: 232–4, 1970.

[2] F. S. K. MacMillian, H. H. Reller and F. H. Synder, "The Antiperspirant Action of Topically Applied Anticholinergics," J. Invest. Derm. 43: 363–7, 1964.

Scopolamine acid salts and the $C_4$–$C_{12}$ esters of scopolamine have been applied topically as antiperspirants. The $C_4$–$C_{12}$ scopolamine esters are reported to be more effective antiperspirants than scopolamine itself because they penetrate better. These esters are the subject of U.S. Pat. No. 3,767,786. They were tested an antiperspirants by applying them as solutions or creams to the forearm and axilla at a does of 2 mg. Minor systemic responses were observed. Such responses were correlated with systemic responses obtained by administering the esters subcutaneously and it was estimated therefrom that only 5% to 10% of the dermally applied esters was absorbed.

The above mentioned patent suggests using mineral oil as a vehicle for antiperspirant compositions containing the esters, provided there is sufficient water miscible vehicle also present to provide a medium for absorption by the skin. Various surfactants are reported as absorption enhancers for the scopolamine esters.

SUMMARY OF THE INVENTION

The invention is a method for administering scopolamine base transdermally to inhibit emesis and nausea for a prolonged time without evoking intolerable side effects, and a therapeutic system, in the form of a bandage, by which the method may be practiced. This therapeutic system incorporates the scopolamine in a programmed dosage form that administers the scopolamine at a predetermined rate over an extended time period.

Specifically, the method comprises administering scopolamine base to unbroken skin in an initial pulse of about 10 to about 200 $\mu g/cm^2$ of skin, and thereafter at a substantially constant rate of about 0.3 to 15 $\mu g/hr$ until a total of about 0.1 to about 2.5 mg scopolamine base have been administered. The bandage for carrying out the above described method comprises a sandwich-type laminate comprising: a backing layer that is substantially impermeable to scopolamine base, one face of which forms the top of the bandage, a scopolamine reservoir layer adjacent to the opposite face of the backing layer comprising about 0.2 to about 3 mg scopolamine base dispersed in a gelled mixture of mineral oil of about 10 to about 100 cp at 25° C. and polyisobutene; a microporous membrane layer adjacent and below the scopolamine reservoir layer through which scopolamine is released from the reservoir layer at a substantially constant rate in the range of about 0.3 $\mu g$ to about 15 $\mu g$ scopolamine base per hour after the bandage is affixed to the skin; and a contact adhesive layer adjacent and below the microporous membrane layer by which the bandage is affixed to the skin comprising 10 to 200 $\mu g$ scopolamine base per $cm^2$ of effective surface area of the bandage dispersed in a gelled mixture of said mineral oil and said polyisobutene. The above range for the constant rate portion of scopolamine administration represents the average scopolamine release rate following the initial two hours of administration.

As used herein the term "effective surface area" means the surface area of the bandage that contacts the skin and through which scopolamine is administered to the skin. As used herein in connection with describing the constant rate portion of the invention method and the rate at which scopolamine is released from said reservoir layer, the term "substantially" indicates that the rate may vary ±30%. Such variation may be inherent in the manufacturing procedure, or be caused by temperature fluctuation, poor affixation of the bandage to the skin, and the like.

BRIEF DESCRIPTION OF THE DRAWINGS

The drawing is an enlarged, schematic, cross-sectional view of the preferred embodiment of the bandage of the invention.

DETAILED DESCRIPTION OF THE INVENTION

The invention resides in the discovery of how to administer scopolamine transdermally to effectively inhibit nausea and emesis without eliciting intolerable parasympatholytic side effects. It involves delivering scopolamine base to the plasma in a controlled manner according to a precise dosage program consisting of an initial pulse administration followed by administration at a substantially constant rate until a desired total quantity of scopolamine has been administered.

Emesis and nausea may be induced by pregnancy, vestibular disturbances (e.g., those caused by motion), radiation treatment, drug treatment (e.g., cancer chemotherapy) or treatment with anesthetics. Such illness may be inhibited by the method of this invention.

The purpose of the pulse portion of the dosage program is to shorten the time it takes for the scopolamine concentration in the plasma to reach the level required for preventive therapy. It partially does this by "saturating" the skin with scopolamine. In this respect the skin initially acts as a "sink" rather than as a "conduit", with most of the scopolamine being bound within the skin and not passing through to circulation. However, once the skin is "saturated", that is the binding sites are occupied, it permits additional scopolamine to pass through circulation. Thus the amount of scopolamine administered in the pulse is a function of the area of skin being treated. A pulse of 10 to 200 $\mu g$ scopolamine per $cm^2$ of skin being teated will usually allow the therapeutic level in the plasma to be reached within about 2-3 hr. Accordingly, an adequate time margin of safety is provided if administration is begun at least about 3 hr before illness is expected. In most instances the pulse will be in the range of 50 to 150 $\mu g$ scopolamine per $cm^2$ of skin being treated. Alternatively the pulse may be expressed in terms of the average release rate per unit of effective surface area over the first two hours of administration. Expressed in this manner in most instances the pulse will be in the range of 20 to 60 $\mu g/hr/cm^2$. The concentration of scopolamine in the plasma can be related to the concentration of free scopolamine in the urine if the glomerular filtration rate of the subject is known, and it is convenient to express the quantity of scopolamine in the plasma in terms of a urinary excretion rate. An average urinary excretion rate of about 0.3 $\mu g$ free scopolamine per hr was found to generally correspond to a therapeutic plasma level. However, it was also found that this rate is subject to about a $\pm 5\%$-fold biological variation. Therefore, the rate ranges between about 0.05 and about 1.5 $\mu g$ per hr depending on the individual.

The purpose of the substantially constant rate administration portion of the method is to supplement, if necessary, the pulse administration in delivering enough scopolamine to reach the above mentioned therapeutic level and to hold that level for as long as is necessary. It follows that the constant rate administration portion will proceed for as long as therapy is required. In this regard a total (including the pulse) of 0.1 to 2.5 mg scopolamine administered in accordance with the above described dosage program will provide a therapeutic effect for about 3 hours to 7 days. It also follows that the level of constant rate administration may vary depending on the body weight (plasma volume) of the patient. In this regard in most instances the rate will be in the range of 5 to 15 $\mu g$ per hr for adults and 3 to 10 $\mu g$ per hr for children (measured as the average rate after 2 hr of administration i.e. after the initial 2 hr of pulse administration).

The skin location at which the method is carried out is important for the reliability and reproducibility of the method. This is because the histology, thickness and vascularization of skin varies from individual to individual as well as from body site to body site on a given individual, and such variance affects the efficacy with which scopolamine may be delivered to the plasma. Applicants have found that the effect of this variance may be substantially eliminated in either of two ways.

The first way is to carry out the method at a skin site, namely the mastoidal area, where scopolamine permeation does not vary significantly from individual to individual and thus the quantity of scopolamine delivered to the plasma or the rate at which such delivery is made is not significantly different between individuals. The second way is to eliminate the stratum corneum as a quantity-affecting or rate-affecting element by treating the skin at the administration site with a skin permeation enhancing agent. Such treatment will allow the method to be carried out at body sites, such as the arms, legs or torso, other than the mastoidal area. Depending on the particular agent involved, the treatment may occur prior to or simultaneously with the administration of scopolamine base pursuant to the invention method. Likewise, the quantity of agent needed will depend on the particular agent used. In any event, the agent plays the dual role of increasing the permeability of the stratum corneum to scopolamine and decreasing the tendency of the stratum corneum to bind scopolamine. Examples of known agents which may be used are dodecyl pyrrolidone, dimethyl lauramide and dimethyl sulfoxide. All three of these agents may be used in pretreatment applications. The pyrrolidone and lauramide may be applied to the administration site at about 4 to 8 $mg/cm^2$ for approximately an hour and then washed off. They may be administered simultaneously with the scopolamine at approximately the same dosage as the scopolamine. Th sulfoxide is preferably used only as a pre-treatment at doses in the range of 5 to 100 $mg/cm^2$ for approximately one hour, and then washed off.

The drawing depicts a bandage, generally designated 10, that when applied to skin administers scopolamine base according to the prescribed dosage program. Bandage 10 is a five-layer laminte. The top layer 11 is a backing that is substantially impermeable to scopolamine base. Its face 12 forms the top surface of the bandage. Backing 11 serves as a protective covering, keeps the volatile components of the bandage from escaping, and fulfills a support function. Preferably, backing layer 11 is itself a laminate of films of polymer and metal foil such as aluminum foil. Polymers that may be used in the layer are high and low density polyethylene, polypropylene, polyvinylchloride and polyethylene terephthalate.

Below and adjacent to layer 11 is a scopolamine reservoir layer 13. Layer 13 contains about 1 to about 6 mg scopolamine base, the undissolved portion of which is depicted as droplets 14. The scopolamine base contained in layer 13 is delivered to the plasma during the constant administration portion of the invention method. Droplets 14 are dispersed homogeneously in a gelled mixture of mineral oil of about 10 to about 100 cp at 25° C. and a blend of polyisobutene. The oil will usually constitute 35% to 65% by weight of the mixture and the polyisobutene will correspondingly usually constitute 35% to 65% by weight of the mixture. The polyisobutene blend comprises a low molecular weight polyisobutene (35,000–50,000 viscosity average molecular weight) and a high molecular weight polyisobutene (1,000,000–1,500,000 viscosity average molecular weight). Preferred mixtures comprise 35% to 65% mineral oil, 10% to 40% low molecular weight polyisobutene, and 20% to 40% high molecular weight polyisobutene. These oil-polyisobutene mixtures are excellent adhesives and help to hold the bandage together. If they were not good adhesives, other means, such as heat sealing, would have to be used to keep the bandage together.

The mineral oil in layer 13 functions as a carrier for the scopolamine base. Scopolamine base has limited solubility in the mineral oil (approximately 2 mg/ml) and the relative amounts of each in layer 13 are such that the mineral oil is saturated with the base for essentially the entire dispensing lifetime of the bandage.

The next lamina in the bandage is a microporous membrane 15 whose pores are filled with the above described mineral oil. Membrane 15 is the element of the bandage that controls the rate at which the base is released from layer 13. The flux of scopolamine through membrane 15 and the area of membrane 15 must be such that scopolamine is released from reservoir layer 13 to the skin at a substantially constant rate in the range of 0.3 to 15 $\mu$g/hr after the bandage has been put in use. The flux follows Ficks' law. It is a function of the tortuosity, porosity and thickness of the membrane, the concentration gradient of scopolamine base across the membrane and the diffusion coefficient of scopolamine base in the mineral oil. The concentration gradient depends on the scopolamine concentrations in the mineral oil at the opposite sides of the membrane. The diffusion coefficient depends on the mineral oil viscosity and decreases with increasing viscosity. The three properties of the membrane are, of course, constant for any given membrane. Membranes that have porosities from about 0.1 to 0.85, tortuosities from 1 to 10, and thicknesses from $10^{-3}$ to $10^{-2}$ cm may be used. The membrane may be formed from polymers such as polypropylene, polycarbonates, polyvinylchloride, cellulose acetate, cellulose nitrate, and polyacrylonitrile.

Below and adjacent membrane 15 is a contact adhesive lamina 16. Lamina 16 contains 10 to 200 $\mu$g scopolamine base per cm effective surface area. The undissolved portion of the scopolamine is depicted as droplets 17. The scopolamine base in lamina 16 is the pulse dosage of the invention method. The scopolamine is dispersed in the same mineral oil-polyisobutene mixture that is used in layer 13. Lamina 16 is the means by which the bandage is attached to the skin. In this regard the mineral oil-polyisobutene mixture adheres less strongly to skin than it does to the other laminas of the bandage; therefore, the bandage tends to remain intact when it is pulled off the skin.

Prior to use, the bandage also includes a strippable, protective coating 18 that covers lamina 16. Just prior to use, coating 18 is peeled away from lamina 16 and discarded. It may be made from scopolamine-mineral oil impermeable materials such as the polymers from which backing 11 may be made, with the provision that these materials are made strippable, such as by siliconizing.

Bandage 10 may be applied to either mastoidal region and it will administer scopolamine according to the described dosage program without requiring any prior or simultaneous treatment of the region with a skin permeation enhancing agent. As indicated above, if the bandage is applied to a body site other than a mastoidal area, the site should be treated with one or more of the described skin permeation enhancing agents. If simultaneous treatment is desired, the agent may be incorporated into bandage 10. In that instance, layers 13 and 16 will contain effective quantities of such agents.

The size of the bandage is not critical. The bandage will usually be sized to administer scopolamine to an area of skin in the range of 0.5 to 4 cm$^2$. Correlatively, the effective surface area of the bandage will also usually be in the range of 0.5 to 4 cm.

EXAMPLES

The following examples illustrate the invention. They are not intended to limit the scope of the invention in any way. Unless indicated otherwise, parts are by weight.

EXAMPLE 1

A solution of 29.2 parts high molecular weight polyisobutene (sold under the designation Vistanex MML-100, 1,200,000 viscosity average molecular weight), 36.5 parts low molecular weight polyisobutene (sold under the designation Vistanex LM-MS, 35,000 viscosity average molecular weight), 58.4 parts mineral oil (10 cp @ 25° C.), 15.7 parts scopolamine base and 860.2 parts chloroform is solvent cast onto an approximately 65 micron thick backing film of aluminized polyethylene terephthalate (sold under the designation MEDPAR) to form a scopolamine base reservoir layer approximately 50 microns thick. A contact adhesive layer-strippable coating combination is similarly prepared by solvent casting onto a 200 micron thick siliconized, aluminized, polyethylene backed polyethylene terephthalate film a solution of 31.8 parts of said high molecular weight polyisobutene, 39.8 parts of said low molecular weight polyisobutene, 63.6 parts of said mineral oil, 4.6 parts of scopolamine base and 860.2 parts chloroform. The resulting contact adhesive layer is approximately 50 microns thick.

The above described backing-reservoir layer combination is then laminated to one face of a 25 micron thick microporous polypropylene membrane (sold under the designation Celgard 2400) saturated with said mineral oil and the above described contact adhesive layer-strippable coating combination is laminated to the opposite face of the membrane. One cm$^2$ circular, disc-shaped bandages are punch cut from the resulting 5-layer laminate. Each bandage is designed to release an initial 150 $\mu$g/cm$^2$ pulse of scopolamine followed by an essentially constant dosage of 3–3.5 $\mu$g/cm$^2$/hr.

EXAMPLE 2

A solution of 22.3 parts of the high molecular weight polyisobutene described in Example 1, 28.0 parts of the low molecular weight polyisobutene described in Example 1, 44.9 parts mineral oil (66 cp @ 25° C.), 12.8 parts scopolamine base, 8.8 parts dimethyl lauramide and 883.2 parts of chloroform is solvent cast onto the backing film described in Example 1 to form a scopolamine base reservoir layer approximately 50 microns thick. A contact adhesive layer-strippable coating combination is similarly prepared by solvent casting onto the siliconized polyethylene terephthalate film described in Example 1 a solution of 23.5 parts of said high molecular weight polyisobutene, 29.5 parts of said low molecular weight polyisobutene, 47.6 parts mineral oil (66 cp @ 25° C.), 7.8 parts scopolamine base, 9.0 parts dimethyl lauramide and 882.6 parts chloroform. The resulting contact layer is approximately 50 microns thick.

The above-described backing-reservoir layer combination is then laminated to one face of a 25 micron thick microporous polypropylene membrane (sold under the designation Celgard 2400) saturated with said mineral oil and the above described contact adhesive layer-strippable coating combination is laminated to the opposite face of the membrane. Four cm² circular, disc-shaped bandages are punch cut from the resulting 5-layer laminate. Each bandage is designed to release an initial 125 μg/cm² pulse of scopolamine followed by an essentially constant dosage of 2 μg/cm²/hr.

The bandages of Example 2 were tested on a double blind basis as follows. A bandage was applied to the skin behind the ear of 17 subjects prior to exposure to motion at sea. Placebo bandages (no scopolamine present) were similarly applied to 18 subjects. All subjects had a prior history of experiencing motion-induced nausea. Only one of the 17 subjects wearing the bandages of Example 2 became ill to the extent that additional anti-nauseant medication had to be administered while at sea. In contrast, 9 of the subjects wearing the placebo bandages had to receive additional antinauseant medication while at sea.

EXAMPLE 3

Therapeutic systems were made according to the procedure of Example 1 except that: the strippable coating was 127 micron thick siliconized polyethylene terephthalate film and the systems were each 2.5 cm² in area. In vitro tests of these systems showed they released an initial pulse of approximately 200 μg in the first two hours of use and an average of approximately 10 μg/hr thereafter through 72 hr.

Modifications of the above described method and therapeutic systems that are obvious of persons of skill in the medical, chemical and/or pharmaceutical arts are intended to be within the scope of the following claims.

What is claimed is:

1. A method for administering scopolamine transdermally for a prolonged time period comprising administering scopolamine base to a predetermined area of unbroken skin in a skin saturating initial dose of about 10 to about 200 μg/cm² of skin and thereafter at a substantially constant rate in the range of about 0.3 to about 15 μg/hr which rate is sufficient to maintain the urinary excretion of scopolamine in the range of from 0.05 to about 1.5 μg/hr for said prolonged period of time.

2. A method for administering scopolamine transdermally for a prolonged period of time comprising:
   (a) administering scopolamine base to a predetermined area of unbroken skin until sufficient scopolamine has been administered to occupy the scopolamine binding sites associated with said area of skin and;
   (b) after said binding site have been occupied continuously administering scopolamine to said area of skin at a substantially constant rate in the range of about 0.3 to about 15 μg/hr for said prolonged period of time.

3. The method of claim 2 wherein said area of skin is located at the mastoidal area.

4. The method of claim 2 wherein the scopolamine is administered to the skin of a subject suffering from a vestibular disturbance.

5. The method of claim 2 wherein the substantially constant rate is about 5 to 15 μg/hr for adults and 3 to 10 μg/hr for children.

6. The method of claim 3 wherein the substantially constant rate is about 5 to 15 μg/hr for adults and 3–10 μg/hr for children.

7. The method of claim 5 wherein said scopolamine binding sites are saturated by the administration of a dose of about 10 to about 200 μg/cm² of skin.

8. The method of claim 2 wherein the scopolamine is administered to the skin of a pregnant subject.

9. The method of claim 2 wherein the scopolamine is administered to the skin of a subject undergoing chemotherapy.

10. The method of claim 2 wherein the scopolamine is administered to the skin of a subject undergoing radiation therapy.

11. The method of claim 2 wherein the scopolamine is administered to the skin of a subject treated with an anesthetic.

* * * * *